United States Patent [19]

Lantzsch et al.

[11] Patent Number: 4,973,753
[45] Date of Patent: Nov. 27, 1990

[54] PROCESS FOR THE PREPARATION OF HYDROXYBENZALDOXIME O-ETHERS

[75] Inventors: Reinhard Lantzsch; Hans-Ludwig Elbe; Wolf Reiser, all of Wuppertal; Johannes Schmetzer, Pulheim, all of Fed. Rep. of Germany

[73] Assignee: Bayer Aktiengesellschaft, Leverkusen, Fed. Rep. of Germany

[21] Appl. No.: 320,145

[22] Filed: Mar. 7, 1989

Related U.S. Application Data

[63] Continuation of Ser. No. 57,879, Jun. 2, 1987, abandoned.

[30] Foreign Application Priority Data

Jun. 14, 1986 [DE] Fed. Rep. of Germany ....... 3620166

[51] Int. Cl.$^5$ ........................................... C07C 259/00
[52] U.S. Cl. ................................................... 564/256
[58] Field of Search ........................................ 564/286

[56] References Cited

U.S. PATENT DOCUMENTS

| 3,184,510 | 5/1965 | Levy | 564/256 X |
| 4,727,074 | 2/1988 | Budai et al. | 564/256 X |
| 4,739,118 | 4/1988 | Elbe | 564/256 X |

FOREIGN PATENT DOCUMENTS

| 0023890 | 2/1981 | European Pat. Off. |
| 0076370 | 4/1983 | European Pat. Off. |
| 0083010 | 7/1983 | European Pat. Off. |
| 0121701 | 10/1984 | European Pat. Off. |
| 0158159 | 10/1985 | European Pat. Off. |
| 0218123 | 4/1987 | European Pat. Off. |
| 2927117 | 1/1981 | Fed. Rep. of Germany. |

OTHER PUBLICATIONS

McOmie(I), "Protective Groups in Organic Chemistry", pp. 149, 157 and 159 (1973).
Palazzo et al., "Chemical Abstracts", vol. 58, p. 4548a (1963).
Hiraoka, "Studies in Organic Chemistry", 12, pp. 167–168, and 175–176 (1982).
McOmie, "Protective Groups in Organic Chemistry", 96–97 (1973).

Primary Examiner—Robert V. Hines
Attorney, Agent, or Firm—Sprung, Horn, Kramer & Woods

[57] ABSTRACT

Hydroxybenzaldoxime O-ethers of the formula

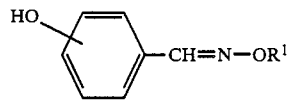

in which
$R^1$ represents alkyl, are obtained by a process in which a tert.-butoxy-benzaldoxime of the formula

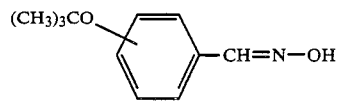

is reacted with alkylating agents of the formula

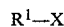

$R^1$—X in which
$R^1$ has the abovementioned meaning and
X represents halogen or $OSO_2OR^1$, wherein
$R^1$ again has the abovementioned meaning, in the presence of a strong base and phase transfer catalyst and in the presence of a diluent at temperatures between 0° C. and 50° C., and the products are then treated with anhydrous acid at temperatures between 0° C. and 50° C., Hydroxybenzaldoxime O-ethers can be used as intermediate products for the synthesis of compounds with a fungicidal, insecticidal and antimycotic activity. The tert.-butoxy-benzalodoxime starting material is a new compound.

3 Claims, No Drawings

PROCESS FOR THE PREPARATION OF HYDROXYBENZALDOXIME O-ETHERS

This is a continuation of application Ser. No. 057,879, filed June 2, 1987, and now abandoned.

The invention relates to a new process for the preparation of known hydroxybenzaldoxime O-ethers which can be used as intermediate products for the synthesis of compounds with a fungicidal, insecticidal and antimycotic activity.

It has already been disclosed that certain hydroxybenzaldoxime O-ethers can be prepared by reacting hydroxybenzaldehydes with the corresponding hydroxylamine derivatives (compare EP-OS (European Published Specification) No. 0,076,370 and EP-OS (European Published Specification) No. 0,115,828). The reaction in question can be illustrated by the following equation:

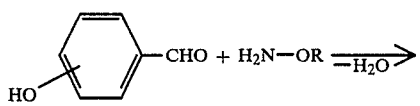

R=alkyl, alkenyl or alkinyl.

Disadvantages of this process are, however, the high cost and poor availability of the substituted hydroxylamines required as reaction components. The use of these substances for production of hydroxybenzaldoxime O-ethers on an industrial scale therefore presents problems.

It is furthermore known that oxime ethers can be prepared in the presence of dipolar aprotic solvents (compare DE-OS (German Published Specification) No. 2,927,117). However, the use of dipolar aprotic solvents on an industrial scale presents problems.

Finally, it is also known that oxime ethers can be synthesized in the presence of alcohols as diluents (compare EP-OS (European Published Specification) No. 0,121,701). Disadvantages of this process are, however, that relatively large amounts of nitrones are formed in side reactions and the yields of the desired products are relatively low.

It has now been found that known hydroxybenzaldoxime O-ethers of the formula

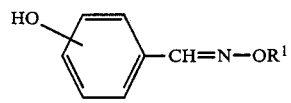

in which
  $R^1$ represents alkyl, are obtained by a process in which tert.-butoxy-benzaldoximes of the formula

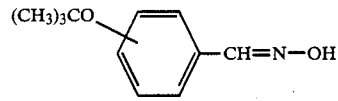

are reacted with alkylating agents of the formula $$R^1 13 X \quad (III)$$

in which
  $R^1$ has the abovementioned meaning and
  X represents halogen or $OSO_2OR^1$, wherein
  $R^1$ again has the abovementioned meaning,
in the presence of a strong base and a phase transfer catalyst and in the presence of a diluent at temperatures between 0° C. and 50° C., and the products are then treated with anhydrous acid at temperatures between 0° C. and 50° C.

It is surprising that the reaction according to the invention proceeds smoothly and with an outstanding yield under the process conditions described. On the basis of the known prior art, it was in fact to be expected that products of the formula

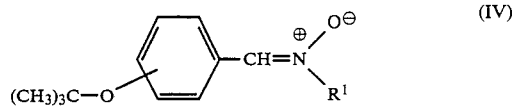

are at least partly formed (compare EP-OS (European Published Specification) No. 0,121,701). It is also unexpected that the tert.-butyl radical can already be split off in the absence of water under very mild conditions, so that the oxime ether radical is not destroyed again in the course of the reaction, which would be feared if water is present (compare EP-OS (European Published Specification) No. 0,083,010).

The process according to the invention is distinguished by a number of advantages. Thus, it enables hydroxybenzaldoxime O-ethers of the formula (I) to be prepared in outstanding yields, readily accessible compounds being employed as starting substances. It is also advantageous that only those diluents which present no problems when used, even on an industrial scale, are required. Furthermore, the solvent does not have to be changed when the process is being carried out. The reaction is moreover easy to carry out at low temperatures, and isolation of the hydroxybenzaldoxime O-ethers of the formula (I) presents no problems at all. The process according to the invention is therefore also particularly suitable for production of hydroxybenzaldoxime O-ethers on an industrial scale.

If, for example, 4-tert.-butoxybenzaldoxime is used as the starting substance, diethyl sulphate is used as the alkylating agent, potassium hydroxide is used as the strong base, tetrabutyl-ammonium bromide is used as the phase transfer catalyst, toluene is used as the diluent and trifluoroacetic acid is used as the acid, the course of the process according to the invention can be illustrated by the following equation:

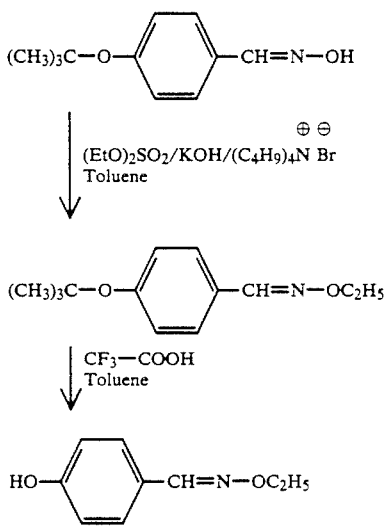

Formula (II) provides a definition of the tert.-butoxybenzaldoximes required as starting substances in carrying out the process according to the invention. Examples of these substances which may be mentioned are 4-tert.-butoxy-benzaldoxime, 3-tert.-butoxy-benzaldoxime and 2-tert.-butoxy-benzaldoxime.

The tert.-butoxy-benzaldoximes of the formula (II) have not yet been disclosed. They can be prepared by a process in which aldehydes of the formula

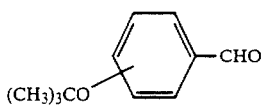
(V)

or acetals thereof are reacted with hydroxylamine or hydroxylamine salts in the presence of a diluent and, if appropriate, in the presence of a catalyst.

The aldehydes of the formula (V) and their acetals are known or can be prepared in a simple manner by processes which are known in principle. Thus, aldehydes of the formula (V) are obtained by a process in which compounds of the formula

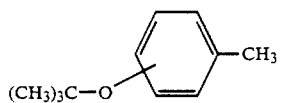
(VI)

are oxidized electrochemically.

The hydroxylamine salts and hydroxylamine furthermore required as starting substances in the above process for the preparation of tert.-butoxy-benzaldoximes of the formula (II) are known. Examples which may be mentioned are hydroxylamine hydrochloride and hydroxylamine sulphate.

Diluents which can be used in the above process for the preparation of tert.-butoxy-benzaldoximes of the formula (II) are all the customary solvents for such reactions. Solvents which are preferably possible are alcohols, such as methanol, ethanol, propanol and butanol, and also mixtures of alcohols and water.

Possible catalysts in the above process for the preparation of tert.-butoxy-benzaldoximes of the formula (II) are all the reaction accelerators customary for such reactions. Accelerators which can preferably be used are salts with a buffer action, such as, for example, sodium acetate, and furthermore weak acids, such as, for example, acetic acid.

The reaction temperatures can be varied within a certain range in the process for the preparation of the tert.-butoxy-benzaldoximes of the formula (II). The reaction is, in general, carried out at temperatures between 0° C. and 50° C., preferably between 20° C. and 40° C.

In carrying out the above process for the preparation of the tert.-butoxy-benzaldoximes of the formula (II), aldehydes of the formula (V) or acetals thereof are reacted with an equivalent amount or an excess of hydroxylamine or hydroxylamine salts, if appropriate, in the presence of a catalyst. Working up is carried out by customary methods.

Formula (III) provides a general definition of the alkylating agents required as reaction components in the process according to the invention. In this formula, $R^1$ preferably represents alkyl with 1 to 10 carbon atoms and X preferably represents chlorine, bromine, iodine or the radical of the formula $-OSO_2OR^1$, wherein $R^1$ again preferably represents alkyl with 1 to 10 carbon atoms.

Particularly preferred substances of the formula (III) are those in which $R^1$ represents alkyl with 1 to 4 carbon atoms and X represents chlorine, bromine or the radical of the formula $-OSO_2OR^1$, wherein $R^1$ again particularly preferably represents alkyl with 1 to 4 carbon atoms.

Examples which may be mentioned of alkylating agents of the formula (III) are: methyl chloride, methyl bromide, dimethyl sulphate, ethyl chloride, ethyl bromide and diethyl sulphate.

The alkylating agents of the formula (III) are known.

Possible strong bases in carrying out the process according to the invention are, preferably, alkali metal hydroxides, such as sodium hydroxide or potassium hydroxide.

Possible phase transfer catalysts in carrying out the process according to the invention are all the customary reaction accelerators of this type. Accelerators which can preferably be used are tetraalkyl-ammonium salts or tetraalkyl-phosphonium salts, such as, for example, tetrabutyl-ammonium bromide.

Possible diluents in carrying out the process according to the invention are, preferably, aromatic hydrocarbons or chlorinated aromatic hydrocarbons. Examples which may be mentioned are toluene, xylenes, chlorobenzene and ortho-dichlorobenzene.

Possible anhydrous acids in carrying out the process according to the invention are, preferably, strong acids. Trifluoroacetic acid, methanesulphonic acid, perfluoroalkanesulphonic acids and hydrogen halides, such as hydrogen chloride and hydrogen bromide, are particularly preferred.

The reaction temperatures can be varied within a certain range in carrying out the process according to the invention. In general, both the actual reaction and the treatment with acid are carried out at temperatures between 0° C. and 50° C., preferably between 10° C. and 30° C.

The reaction according to the invention is, in general, carried out under normal pressure. However, it is also possible for the reaction to be carried out under increased or reduced pressure.

In carrying out the process according to the invention, in general 1 to 2 mol, preferably 1 to 1.5 mol, of alkylating agent of the formula (III) and 1 to 3 mol, preferably 2.1 to 2.5 mol, of base and, if appropriate, a catalytic amount of a phase transfer catalyst are employed per mol of tert.-butoxy-benzaldoxime of the formula (II). Catalytic amounts of acid are sufficient for the subsequent acid treatment; however, an excess of acid can also be employed. If salt formation takes place, at least equimolar amounts of acid must be used.

In general, the process according to the invention is carried out by a procedure in which the reaction mixture obtained after the first reaction is freed from the salts it contains by filtration and the resulting tert.-butoxy-benzaldoxime O-ester is treated with acid either after prior isolation or directly in the presence of a diluent. Subsequent working up is carried out by customary methods. Thus, for example, a procedure can be followed in which water is added to the reaction mixture and the organic phase is separated off, washed with an aqueous basic solution and water in succession and, after drying, is concentrated. If the desired products of the formula (I) are obtained in the form of salts, these can be filtered off from the mixture and converted into the free hydroxy-benzaldoxime O-ethers of the formula (I) by treatment with an aqueous-basic solution.

The hydroxybenzaldoxime O-ethers of the formula (I) which can be prepared by the process according to the invention are generally known starting substances for the synthesis of biologically active compounds, such as, for example, for the synthesis of oxime ethers which have good insecticidal properties (compare EP-OS (European Published Specification) No. 0,115,828); of azolyl-phenoxy derivatives which have outstanding fungicidal properties (compare EP-OS (European Published Specification) No. 0,076,370); of 1-hydroxyethyl-triazolyl derivatives which have good fungicidal and antimycotic properties (compare EP-OS (European Published Specification) No. 0,110,048 and DE-OS (German Published Specification) No. 3,314,548); and of hydroxyalkylazole derivatives which have a good antimycotic activity (compare DE-OS (German Published Specification) No. 3,427,844).

Thus, for example, 3,3-dimethyl-1-(4-methoximinomethyl-phenoxy)-1-(1,2,4-triazol-1-yl)-butan-2-one of the formula

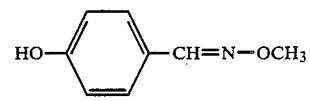

can be prepared by a process in which 3,3-dimethyl-1(1,2,4-triazol-1-yl)-butan-2-one is first reacted with bromine to give 1-bromo-(1,2,4-triazol-1-yl)-3,3-dimethyl- butan-2-one and this is then reacted with 4-hydroxybenzaldehyde O-methyl-oxime ether in the presence of a base. This synthesis can be illustrated by an equation as follows:

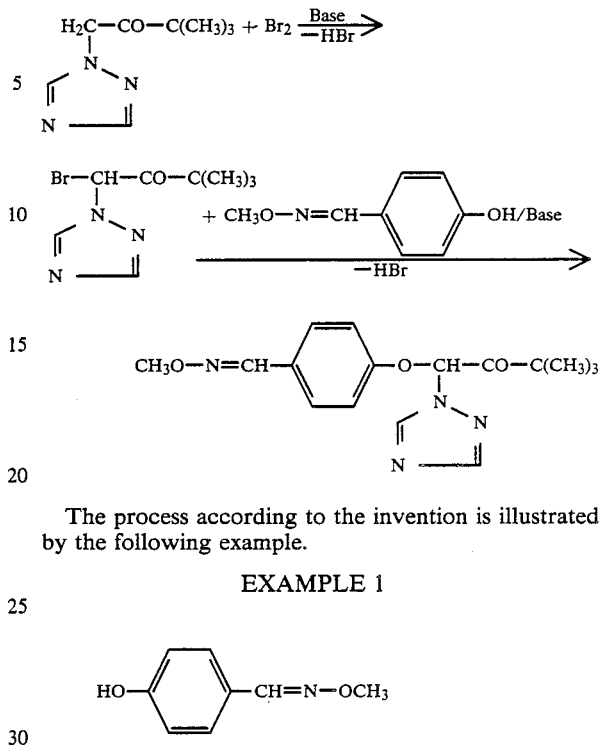

The process according to the invention is illustrated by the following example.

EXAMPLE 1

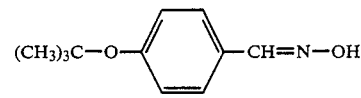

14 g (0.25 mol) of potassium hydroide are added to a solution of 48 g of a product consisting of 4-tert.butoxybenzaldoxime to the extent of 90.2% by weight (=0.224 mol) and 2 g of tetrabutylammonium bromide in 500 ml of toluene at room temperature. The mixture is stirred at 20-25° C for a further 15 minutes, 35 g (0.228 mol) of dimethyl sulphate are then added dropwise at this temperature and the mixture is subsequently stirred for 12 hours. The resulting salts are then filtered off and an excess of hydrogen chloride is passed into the reaction mixture. Thereafter, the mixture is stirred at 20-25° C. for 4 hours and filtered. 38.7 g (92% of theory) of 4-hydroxy-benzaldoxime O-methyl ether are obtained in this manner in the form of the hydrochloride.

Melting point 148° C.

The hydrochloride is converted into 4-hydroxybenzaldoxime O-methyl ether by treatment with aqueous sodium bicarbonate solution.

Yield: quantitative

Boiling point 116° C. /0.05 mbar

Preparation of the starting substance:

$(CH_3)_3C-O-\phantom{a}\text{C}_6\text{H}_4\phantom{a}-CH=N-OH$ 89 g of 4-tert.-butoxy-benzaldehyde are added dropwise to a solution of 38.3 g of hydroxylamine hydrochloride and 45 g of sodium acetate in 700 ml of methanol and 35 ml of water, with stirring. When the slightly exothermic reaction has subsided, the mixture is subsequently stirred at 20-25° C. for 12 hours and filtered and the filtrate is concentrated under reduced pressure. The residue is taken up in methylene chloride and the resulting organic phase is washed with aqueous sodium bicarbonate solution and water in succession. After drying and concentrating under reduced pressure, 95.8 g of a crystalline substance of melting point 70-75°C. remain. According to the gas chromatogram, the product consists of 4- tert.butoxy-benzaldoxime (syn+anti) to the extent of 90.2% by weight. The yield is accordingly calculated as 89.5% of theory. Example 2

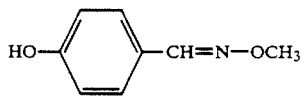

20.7 g (0.1 mol) of 4-tert.-butoxy-benzaldoxime O-methyl ether are dissolved in 200 ml of toluene, and 20 ml of trifluoroacetic acid are added. The reaction mixture is stirred at room temperature for 12 hours and then poured into water and the organic phase is separated off. The aqueous phase is extracted a further three times with methylene chloride. The combined organic phases are washed with aqueous sodium bicarbonate solution and water in succession and then dried and concentrated under reduced pressure. 13 g (86% of theory) of 4-hydroxybenzaldoxime O-methyl ether are obtained in this manner.

Boiling point 112-114° C./0.05 mbar

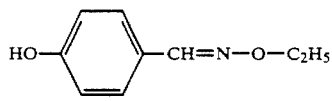

4-tert.-butoxy-benzaldoxime is reacted with diethyl sulphate by the method described in Example 1. Working up is likewise carried out by the method described in Example 1. 4-Hydroxy-benzaldoxime O-ethyl ether is obtained in this manner in the form of a solid substance of melting point 64° C.

Example 4

Preparation of the compound of the formula

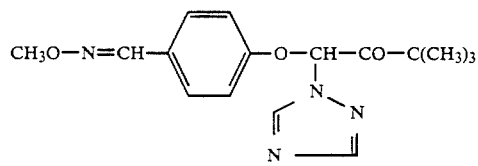

110 g (1.34 mol) of sodium acetate are introduced into a solution of 217 g (1.3 mol) of 3,3-dimethyl-1(1,2,4-triazol-1-yl)-2-butanone in 700 ml of glacial acetic acid, whereupon the temperature rises to about 28° C. The mixture is subsequently stirred for 30 minutes and 208 g (1.3 mol) of bromine are added dropwise at 30 to 33° C., with gentle cooling. The reaction mixture is subsequently stirred at room temperature for 2.5 hours and poured into 1,200 ml of water. It is extracted with methylene chloride and the product is washed with water and aqueous bicarbonate solution, dried over sodium sulphate and concentrated.

The crude 1-bromo-3,3-dimethyl-1-(1,2,4-triazol-1-yl)-2-butanone thus obtained is dissolved in 100 ml of acetonitrile and the solution is added to a suspension of 151 g (1 mol) of 4-hydroxy-benzaldoxime O-methyl ether and 150 g (1.09 mol) of potassium carbonate in 800 ml of acetonitrile, whereupon the temperature rises to about 40° C. The reaction mixture is subsequently stirred at 60° to 65° C. for 3 hours and then cooled and poured onto water. It is extracted with toluene and the product is washed with water, dried and concentrated. The residue is triturated in ligroin and dried on clay. 241 g (76% of theory) of 3,3- dimethyl-1-(4-methoximinomethylphenoxy)-1-(1,2,4-triazol-1-yl) -butan-2-one of melting point 83-87 °C. are obtained.

We claim:

1. A process for the preparation of a hydroxybenzaldoxime O-ether of the formula

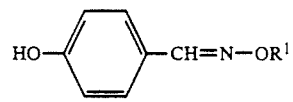

in which
R¹ represents alkyl with 1 to 10 carbon atoms,
wherein a tert.-butoxy-benzaldoxime of the formula

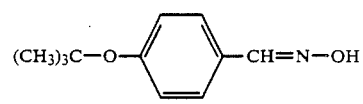

is reacted with an alkylating agent of the formula

R¹—X in which and
R¹ has the abovementioned meaning
X represents halogen or OSO₂OR¹,
wherein
R¹ has the abovementioned meaning, in the presence of an alkali metal hydroxide, in the presence of a phase transfer catalyst selected from tetraalkylammonium salts and tetraalkylphosphonium salts, and in the presence of a diluent selected from aromatic hydrocarbons and chlorinated aromatic hydrocarbons, at temperatures between 0° C. and 50° C., and the products are then treated with an anhydrous acid selected from trifluoractive acid, methanesulphonic acid, perfluoroalkanecarboxylic acid and hydrogen halide, at a temperature between 0° C. and 50° C.

2. Process according to claim 1, wherein the alkylating agent employed
R¹ represents alkyl with 1 to 10 carbon atoms and
X represents chlorine, bromine, iodine or the radical of the formula —OSO₂OR¹,
wherein
R¹ again represents alkyl with 1 to 10 carbon atoms.

3. A process according to claim 1, wherein the reaction carried out at temperatures between 10° C. and 30° C.

* * * * *